(12) United States Patent (10) Patent No.: US 8,703,454 B2
Schalk et al. (45) Date of Patent: Apr. 22, 2014

(54) METHOD FOR PRODUCING (+)-ZIZAENE

(75) Inventors: Michel Schalk, Collonges-Sous-Saleve (FR); Fabienne Deguerry, Geneva (CH)

(73) Assignee: Firmenich SA, Geneva (CH)

( * ) Notice: Subject to any disclaimer, the term of this patent is extended or adjusted under 35 U.S.C. 154(b) by 18 days.

(21) Appl. No.: 13/258,193

(22) PCT Filed: May 12, 2010

(86) PCT No.: PCT/IB2010/052103
§ 371 (c)(1),
(2), (4) Date: Sep. 21, 2011

(87) PCT Pub. No.: WO2010/134004
PCT Pub. Date: Nov. 25, 2010

(65) Prior Publication Data
US 2012/0021475 A1 Jan. 26, 2012

(30) Foreign Application Priority Data

May 20, 2009 (WO) .................. PCT/IB2009/052118

(51) Int. Cl.
*C12P 5/00* (2006.01)
*C12N 9/00* (2006.01)
(52) U.S. Cl.
USPC .......................................... 435/166; 435/183
(58) Field of Classification Search
None
See application file for complete search history.

(56) References Cited

U.S. PATENT DOCUMENTS

| 2008/0268500 A1 | 10/2008 | Schalk | 435/69.1 |
| 2009/0313718 A1 | 12/2009 | Degenhardt et al. | 800/265 |

FOREIGN PATENT DOCUMENTS

| EP | 1 878 792 A1 | 1/2008 |
| WO | WO 2006/134523 A2 | 12/2006 |
| WO | WO 2009/109597 A1 | 9/2009 |

OTHER PUBLICATIONS

International Search Report and Written Opinion of the International Searching Authority for application No. PCT/IB2010/052103, mailed Aug. 3, 2010.
Altschul et al., "Basic Local Alignment Search Tool," J. Mol. Biol., 215:403-410 (1990).
Altschul, "Amino Acid Substitution Matrices from an Information Theoretic Perspective," J. Mol. Biol., 219:555-565 (1991).
Asadollahi et al., "Production of Plant Sesquiterpenes in *Saccharomyces cerevisiae*: Effect of ERG9 Repression on Sesquiterpene Biosyntheis," Biotechnology and Bioengineering, 99(3):666-677 (2008).
Barker et al., "Synthetic Photochemistry. A New Synthesis of (±)-Zizaene via an Intramolecular Variant of the de Mayo Reaction," J. Chem. Soc., Perkin Trans. 1, 1901-1904 (1983).
Chandra Pati et al., "A stereocontrolled total synthesis of (±)-zizaene," Tetrahedron, 58:1773-1778 (2002).
Del Gludice et al., "The microbial community of Vetiver root and its involvement into essential oil biogenesis," Environmental Microbiology, 10(10):2824-2841 (2008).
Hernandez et al., "De novo bacterial genome sequencing: Millions of very short reads assembled on a desktop computer," Genome Research, 18:802-809 (2008).
Hong et al., "Consequences of Conformational Preorganization in Sesquiterpene Biosynthesis: Theoretical Studies on the Formation of the Bisabolene, Curcumene, Acoradiene, Zizaene, Cedrene, Duprezianene, and Sesquithuriferol Sesquiterpenes," J. Am. Chem. Soc., 131:7999-8015 (2009).
Keller, "Rapid synthesis of isoprenoid diphosphates and their isolation in one step using either thin layer or flash chromatography," Journal of Chromatography, 645:161-167 (1993).
Kolosova et al., "Isolation of high-quality RNA from gymnosperm and angiosperm trees," BioTechniques, 35:821-824 (May 2004).
Lin et al., "Genome Mining in *Streptomyces coelicolor*: Molecular Cloning and Characterization of a New Sesquiterpene Synthase," J. Am. Chem. Soc., 128:6022-6023 (2006).
Martin et al., "Engineering a mevalonate pathway in *Escherichia coli* for production of terpenoids," Nature Biotechnology, 21(7):796-802 (2003).
Schardl et al., "Design and construction of a versatile system for the expression of foreign genes in plants," Gene, 61(1):1-11 (1987).
Stemmer, "DNA shuffling by random fragmentation and reassembly: In vitro recombination for molecular evolution," Proc. Natl. Acad. Sci. USA, 91:10747-10751 (1994).
Takahashi et al., "Metabolic Engineering of Sesquiterpene Metabolism in Yeast," Biotechnology and Bioengineering, 97:170-181 (2007).
Tatusova et al., "BLAST 2 Sequences, a new tool for comparing protein and nucleotide sequences," FEMS Microbiology Letters, 174:247-250 (1999).
Weyerstahl et al., "Constituents of Haitian vetiver oil," Flavour and Fragrance Journal, 15:395-412 (2000).
Wu et al., "Redirection of cytosolic or plastidic isoprenoid precursors elevates terpene production in plants," Nature Biotechnology, 24(11):1441-1447 (2006).
Zerbino et al., "Velvet: Algorithms for de novo short read assembly using de Bruijn graphs," Genome Research, 18:821-829 (2008).

*Primary Examiner* — Suzanne M Noakes

(57) ABSTRACT

A method of producing (+)-zizaene by contacting at least one polypeptide with farnesyl pyrophosphate (FPP) in vitro or in vivo to produce (+)-zizaene, a compound which can be used as precursor for diverse compounds useful in the fields of perfumery and flavoring. An amino acid sequence of a polypeptide useful in the method, a nucleic acid encoding the polypeptide of the invention, an expression vector containing the nucleic acid and a non-human host organism or a cell transformed to be used in the method of producing (+)-zizaene are also disclosed.

16 Claims, 3 Drawing Sheets

(+)-zizaene prezizaene

α-funebrene

β-funebrene

SEQUENCE LISTING

<160> NUMBER OF SEQ ID NOS: 17

<210> SEQ ID NO 1
<211> LENGTH: 555
<212> TYPE: PRT
<213> ORGANISM: Vetiveria zizanoides

<400> SEQUENCE: 1

```
Met Ala Thr Thr Ala Ala Phe Cys Leu Thr Thr Thr Pro Ile Gly Glu
1               5                   10                  15

Pro Val Cys Arg Arg Gln Tyr Leu Pro Thr Val Trp Gly Ser Phe Phe
            20                  25                  30

Leu Thr Tyr Gln Pro Cys Thr Pro Glu Glu Val Gln Ser Met Glu Glu
        35                  40                  45

Arg Ala Leu Ala Lys Lys Thr Glu Val Gly Arg Met Leu Gln Glu Val
    50                  55                  60

Ala Ala Ser Ser Asn Leu Ala Arg Lys Leu Gly Leu Val Asp Glu Leu
65                  70                  75                  80

Glu Arg Leu Gly Val Asp Tyr His Tyr Lys Thr Glu Ile Asn Asp Leu
                85                  90                  95

Leu Gly Ala Ile Tyr Asn Gly Lys Asp Asp Asp Asn Gly Gly Ser Asp
            100                 105                 110

Asp Asp Leu Tyr Ile Thr Ser Leu Lys Phe Tyr Leu Leu Arg Lys His
        115                 120                 125

Gly Tyr Ala Leu Ser Ser Asp Val Phe Leu Lys Phe Arg Asp Glu Gln
    130                 135                 140

Gly Asn Ile Ser Ser Asp Asp Val Lys Cys Leu Ile Met Leu Tyr Asp
145                 150                 155                 160

Ala Ser His Leu Arg Ile His Glu Glu Lys Ile Leu Asp Asn Ile Asn
                165                 170                 175

Ser Phe Thr Lys Ser Cys Leu Gln Ser Val Leu Glu Thr Asn Leu Glu
            180                 185                 190

Pro Ala Leu Gln Glu Glu Val Arg Cys Thr Leu Glu Thr Pro Arg Phe
        195                 200                 205

Arg Arg Val Glu Arg Ile Glu Ala Lys Arg Phe Ile Ser Ala Tyr Glu
    210                 215                 220

Lys Asn Ile Ala Arg Asp Asp Ala Leu Leu Glu Phe Ala Arg Leu Asp
225                 230                 235                 240

Tyr Asn Ile Val Gln Ile Leu Tyr Cys Lys Glu Leu Lys Glu Leu Thr
                245                 250                 255

Val Trp Trp Lys Glu Phe His Ser Arg Thr Asn Leu Thr Phe Ala Arg
            260                 265                 270

Asp Arg Ile Val Glu Met Tyr Phe Trp Val Met Ala Ile Ile Tyr Glu
        275                 280                 285

Pro Cys Tyr Ser Tyr Ser Arg Ile Trp Val Thr Lys Met Phe Leu Ser
    290                 295                 300

Val Ala Leu Leu Asp Asp Ile Tyr Asp Asn Tyr Thr Ser Thr Glu Glu
305                 310                 315                 320

Ser Asn Ile Phe Thr Thr Ala Met Glu Arg Trp Asp Val Lys Ala Thr
                325                 330                 335

Glu Gln Leu Pro Ala Asn Met Arg Thr Phe Tyr Asp Tyr Leu Ile Cys
            340                 345                 350

Thr Thr Asp Glu Val Val Glu Gly Leu Lys Leu Gln Asn Asn Lys Asn
        355                 360                 365
```

```
Ala Glu Leu Val Lys Lys Val Leu Ile Asp Ala Ala Lys Cys Tyr His
    370                 375                 380

Ser Glu Val Lys Trp Arg Asp Asp His Tyr Val Pro Asn Asp Val Gly
385                 390                 395                 400

Glu His Leu Gln Leu Ser Met Arg Ser Ile Ala Ala Met His Ser Ile
                405                 410                 415

Asn Phe Val Phe Ile Ser Leu Gly Ala Val Cys Thr Arg Glu Ala Val
            420                 425                 430

Glu Cys Ala Phe Thr Tyr Pro Lys Ile Ile Arg Gly Ile Cys Val His
        435                 440                 445

Ala Arg Ile Ser Asn Asp Ile Ala Ser His Glu Arg Glu Gln Ala Ser
    450                 455                 460

Glu His Met Ala Ser Thr Leu Gln Thr Cys Met Lys Gln Tyr Gly Ile
465                 470                 475                 480

Thr Val Glu Glu Ala Ala Glu Lys Leu Arg Val Ile Asn Glu Glu Ser
                485                 490                 495

Trp Met Asp Ile Val Glu Glu Cys Leu Tyr Lys Asp Gln Tyr Pro Leu
            500                 505                 510

Ala Leu Ser Glu Arg Val Val Ala Phe Ala Gln Ser Ile Cys Phe Met
        515                 520                 525

Tyr Asn Gly Val Asp Lys Tyr Thr Ile Pro Ser Lys Leu Lys Asp Ser
    530                 535                 540

Leu Asp Ser Leu Tyr Val Asn Leu Ile Pro Val
545                 550                 555

<210> SEQ ID NO 2
<211> LENGTH: 1668
<212> TYPE: DNA
<213> ORGANISM: Vetiveria zizanoides

<400> SEQUENCE: 2
atggcgacga ctgccgcctt ctgcctcacc accactccga tcggcgagcc agtctgtcgc    60
cggcagtacc tcccaaccgt ctggggcagc ttcttcctca cctaccagcc atgcacgccg   120
gaagaggtcc agtccatgga ggagagggct ctggccaaga gacggaggt ggggcgcatg    180 ttgcaggagg tcgccgcctc cagtaacctc gcacggaagc tgggccttgt cgatgagcta   240
gagcggctcg gggtggacta tcactacaag acggagatca cgacttgct gggtgccatt    300 tataatggca aggacgacga taatggaggt tctgatgacg acctctatat cacatcgctt   360
aagttctatc tgctcaggaa gcatgggtac gctttatctt cagatgtgtt tctgaagttc   420
agagatgagc aaggaaatat ttcaagtgat gatgtgaaat gcctgatcat gttgtatgat   480
gcctcacatt tgaggattca tgaggagaaa attcttgaca catcaacag tttcaccaag    540 agctgcctcc aatcagtttt agaaacaaat ttggaaccgg ctctccaaga ggaggtgcgg   600
tgcacattgg agacacctcg attcagaagg gttgagagaa tcgaagcgaa acgctttatc   660
tcagcgtacg aaaagaacat agcacgagat gacgccctac tagagtttgc aaggctggac   720
tacaatatcg tgcaaattct ctactgcaag gagctgaaaa aacttacagt atggtggaag   780
gagttccatt cacggacaaa tctgacattt gcacgagata gaattgtgga gatgtatttc   840
tgggtcatgg caattattta cgagccttgt tactcgtatt cacggatatg ggttacaaaa   900
atgtttctat ccgtggcatt gttggatgac atctatgaca attatacgag cacagaggag   960
agcaatatct ttactacggc catggaaagg tgggatgtga aggccaccga caaactgcca  1020
gcaaacatga ggacattcta cgattactta atttgtacaa cagatgaggt cgtagaagaa  1080
```

-continued

```
ttgaaacttc agaataataa gaatgctgaa ttagtcaaga aagtgctgat tgacgccgct   1140
aaatgctacc attcggaggt caaatggcgt gatgaccact acgtccctaa tgatgttgga   1200
gagcacctgc agctttcaat gcgaagcatt gcagctatgc actccatcaa ctttgtcttc   1260
atttcactgg gagctgtgtg tactagggag gcggttgagt gtgctttcac ttatccaaaa   1320
attattagag gtatatgtgt tcacgcacgt attagtaacg atatcgcgtc acatgagcga   1380
gaacaagctt cggagcatat ggcatcaacg ttgcaaactt gcatgaagca gtatgggatt   1440
acagtagagg aagctgctga aaagctcaga gtaataaacg aggagtcatg gatggacatc   1500
gttgaggaat gcctttataa ggaccagtat cccctggcgc tttcggagag ggtggtggct   1560
tttgcacaat caatatgttt catgtacaat ggtgtagata aatacaccat accatcaaaa   1620
ctcaaggaca gtctagactc attgtacgtc aatttgattc cagtttga                1668
```

<210> SEQ ID NO 3
<211> LENGTH: 1090
<212> TYPE: DNA
<213> ORGANISM: Vetiveria zizanoides

<400> SEQUENCE: 3

```
tgtgaaatgc ctgatcatgt tgtatgatgc ctcacatttg aggattcatg aggagaaaat     60
tcttgacaac atcaacagtt tcaccaagag ctgcctccaa tcagttttag aaacaaattt    120
ggaaccggct ctccaagagg aggtgcggtg cacattggag acacctcgat tcagaagggt    180
tgagagaatc gaagcgaaac gctttatctc agcgtacgaa aagaacatag cacgagatga    240
cgccctacta gagtttgcaa ggctggacta caatatcgtg caaattctct actgcaagga    300
gctgaaagaa cttacagtat ggtggaagga gttccattca cggacaaatc tgacatttgc    360
acgagataga attgtggaga tgtatttctg ggtcatggca attatttacg agccttgtta    420
ctcgtattca cggatatggg ttacaaaaat gtttctatcc gtggcattgt tggatgacat    480
ctatgacaat tatacgagca cagaggagag caatatcttt actacggcca tggaaaggtg    540
ggatgtgaag gccaccgaac aactgccagc aaacatgagg acattctacg attacttaat    600
ttgtacaaca gatgaggtcg tagaagaatt gaaacttcag aataataaga atgctgaatt    660
agtcaagaaa gtgctgattg acgccgctaa atgctaccat tcggaggtca aatggcgtga    720
tgaccactac gtccctaatg atgttggaga gcacctgcag ctttcaatgc gaagcattgc    780
agctatgcac tccatcaact ttgtcttcat ttcactggga gctgtgtgta ctagggaggc    840
ggttgagtgt gctttcactt atccaaaaat tattagaggt atatgtgttc acgcacgtat    900
tagtaacgat atcgcgtcac atgagcgaga acaagcttcg gagcatatgg catcaacgtt    960
gcaaacttgc atgaagcagt atgggattac agtagaggaa gctgctgaaa agctcagagt   1020
aataaacgag gagtcatgga tggacatcgt tgaggaatgc ctttataagg accagtatcc   1080
cctggcgctt                                                          1090
```

<210> SEQ ID NO 4
<211> LENGTH: 29
<212> TYPE: DNA
<213> ORGANISM: Artificial sequence
<220> FEATURE:
<223> OTHER INFORMATION: Primer

<400> SEQUENCE: 4

```
catagcacga gatgacgccc tactagagt                                       29
```

```
<210> SEQ ID NO 5
<211> LENGTH: 26
<212> TYPE: DNA
<213> ORGANISM: Artificial sequence
<220> FEATURE:
<223> OTHER INFORMATION: Primer

<400> SEQUENCE: 5
gcaaggctgg actacaatat cgtgca                                           26

<210> SEQ ID NO 6
<211> LENGTH: 28
<212> TYPE: DNA
<213> ORGANISM: Artificial sequence
<220> FEATURE:
<223> OTHER INFORMATION: Primer

<400> SEQUENCE: 6
cggtggcctt cacatcccac ctttccat                                         28

<210> SEQ ID NO 7
<211> LENGTH: 28
<212> TYPE: DNA
<213> ORGANISM: Artificial sequence
<220> FEATURE:
<223> OTHER INFORMATION: Primer

<400> SEQUENCE: 7
aagatattgc tctcctctgt gctcgtat                                         28

<210> SEQ ID NO 8
<211> LENGTH: 1925
<212> TYPE: DNA
<213> ORGANISM: Vetiveria zizanoides

<400> SEQUENCE: 8
gaagcaaagc catctgccgt gctatcactc tagcaaatta tactgagtgg ataaacttaa       60
taccacacca gacgttttgc attcatggcg acgactgccg ccttctgcct caccaccact      120
ccgatcggcg agccagtctg tcgccggcag tacctcccaa ccgtctgggg cagcttcttc      180
ctcacctacc agccatgcac gccggaagag gtccagtcca tggaggagag ggctctggcc      240
aagaagacgg aggtggggcg catgttgcag gaggtcgccg cctccagtaa cctcgcacgg      300
aagctgggcc ttgtcgatga gctagagcgg ctcggggtgg actatcacta caagacggag      360
atcaacgact tgctgggtgc catttataat ggcaaggacg acgataatgg aggttctgat      420
gacgacctct atatcacatc gcttaagttc tatctgctca ggaagcatgg gtacgcttta      480
tcttcagatg tgtttctgaa gttcagagat gagcaaggaa atatttcaag tgatgatgtg      540
aaatgcctga tcatgttgta tgatgcctca catttgagga ttcatgagga gaaaattctt      600
gacaacatca acagtttcac caagagctgc ctccaatcag ttttagaaac aaatttggaa      660
ccggctctcc aagaggaggt gcggtgcaca ttggagacac ctcgattcag aagggttgag      720
agaatcgaag cgaaacgctt tatctcagcg tacgaaaaga acatagcacg agatgacgcc      780
ctactagagt ttgcaaggct ggactacaat atcgtgcaaa ttctctactg caaggagctg      840
aaagaactta cagtatggtg gaaggagttc cattcacgga caaatctgac atttgcacga      900
gatagaattg tggagatgta tttctgggtc atggcaatta tttacgagcc ttgttactcg      960
tattcacgga tatgggttac aaaaatgttt ctatccgtgg cattgttgga tgacatctat     1020
gacaattata cgagcacaga ggagagcaat atctttacta cggccatgga aagtgggat      1080 gtgaaggcca ccgaacaact gccagcaaac atgaggacat tctacgatta cttaatttgt     1140
```

| | | | |
|---|---|---|---|
| acaacagatg aggtcgtaga agaattgaaa cttcagaata ataagaatgc tgaattagtc | | | 1200 |
| aagaaagtgc tgattgacgc cgctaaatgc taccattcgg aggtcaaatg gcgtgatgac | | | 1260 |
| cactacgtcc ctaatgatgt tggagagcac ctgcagcttt caatgcgaag cattgcagct | | | 1320 |
| atgcactcca tcaactttgt cttcatttca ctgggagctg tgtgtactag ggaggcggtt | | | 1380 |
| gagtgtgctt tcacttatcc aaaaattatt agaggtatat gtgttcacgc acgtattagt | | | 1440 |
| aacgatatcg cgtcacatga gcgagaacaa gcttcggagc atatggcatc aacgttgcaa | | | 1500 |
| acttgcatga agcagtatgg gattacagta gaggaagctg ctgaaaagct cagagtaata | | | 1560 |
| aacgaggagt catggatgga catcgttgag gaatgccttt ataaggacca gtatcccctg | | | 1620 |
| gcgctttcgg agagggtggt ggcttttgca caatcaatat gtttcatgta caatggtgta | | | 1680 |
| gataaataca ccataccatc aaaactcaag gacagtctag actcattgta cgtcaatttg | | | 1740 |
| attccagttt gacgacatcg catcaagtat taattctagg cttaatataa tgccagtaaa | | | 1800 |
| catcatatgt aagggatatt tactttcgtg aatccaaata atttgagggg tcctgtgttc | | | 1860 |
| ctcttaccaa ggatatgtca tcaagttgaa aaatatagcc agcaaaaaaa aaaaaaaaa | | | 1920 |
| aaaaa | | | 1925 |

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
caccatggcg acgactgccg ccttct           26

<210> SEQ ID NO 10
<211> LENGTH: 22
<212> TYPE: DNA
<213> ORGANISM: Artificial sequence
<220> FEATURE:
<223> OTHER INFORMATION: Primer

<400> SEQUENCE: 10
cgatgtcgtc aaactggaat ca               22

<210> SEQ ID NO 11
<211> LENGTH: 1671
<212> TYPE: DNA
<213> ORGANISM: Artificial sequence
<220> FEATURE:
<223> OTHER INFORMATION: Redesigned sequence for E. coli obtained from
      SEQ ID NO:8

<400> SEQUENCE: 11

| | | | |
|---|---|---|---|
| atggctacta cggctgcttt tgtctgact actactccta ttggtgagcc ggtgtgtcgt | | | 60 |
| cgccaatacc tgccgactgt gtggggtagc ttcttcttga cctaccaacc gtgcaccccg | | | 120 |
| gaagaggtgc aaagcatgga ggagcgtgca ttggccaaaa agaccgaggt tggccgtatg | | | 180 |
| ttgcaagagg tggcggccag cagcaacctg gcccgcaagc tgggtttggt tgacgagctg | | | 240 |
| gagcgtctgg gtgtggacta ccattacaaa accgagatta cgatctgct gggcgcgatc | | | 300 |
| tataatggta aggacgatga caacggcggt agcgacgatg atctgtacat tacgtctctg | | | 360 |
| aaattctatc tgctgcgtaa gcatggttat gcattgagca gcgatgtttt tctgaaattt | | | 420 |
| cgcgacgagc agggtaacat tagctccgac gacgtcaagt gcctgatcat gttgtacgac | | | 480 |

```
gcgagccact tgcgtattca tgaggagaaa atcctggata atatcaattc cttcacgaag      540
agctgcctgc aaagcgttct ggaaccaat ctggaaccgg cgctgcagga agaggttcgc       600
tgtacgctgg agacgccgcg tttccgccgt gtcgaacgta ttgaagcaaa acgcttcatt      660
agcgcgtacg agaagaacat tgcgcgtgac gacgctctgc tggagttcgc gcgcctggac      720
tacaacattg tccagattct gtattgcaaa gagctgaaag aactgacggt gtggtggaag      780
gagttccaca gccgcaccaa tctgacgttt gcacgtgatc gcatcgtgga aatgtacttt      840
tgggtcatgg caattatcta cgagccttgc tactcgtata gccgcatttg ggtcaccaaa      900 atgttttga gcgtcgcact gctggatgat atttacgaca actatactag cacggaggaa       960
agcaacattt tcaccacggc gatggagcgc tgggacgtga aagcgaccga caactgccg     1020 gcgaatatgc gtacctttta tgactatctg atctgcacca ccgacgaagt tgttgaagaa     1080
ctgaaactgc agaataacaa gaacgcggaa ctggttaaga aggtgctgat cgacgcggcc     1140
aaatgctatc atagcgaagt taatggcgc gacgatcact acgttccgaa tgacgttggt      1200
gaacatctgc agctgtcgat gcgttccatt gcggcgatgc acagcattaa tttcgtgttc     1260
atttccctgg cgccgtgtg tactcgcgag cagtcgaat gcgcgtttac ttatccgaag       1320
atcattcgcg gtatttgtgt ccatgcccgt atctccaatg acattgcctc ccatgagcgc     1380
gagcaggcat ccgagcacat ggctagcact ctgcaaacct gcatgaagca gtatggcatt     1440
accgttgagg aggcggcaga aaaactgcgt gtgattaacg aggagagctg gatggatatc     1500
gtcgaggagt gcctgtacaa ggatcagtat ccgctggcat tgtctgagcg cgtcgttgca     1560
tttgcccaga gcatttgttt tatgtacaat ggcgtggaca agtacaccat tccgagcaag     1620
ctgaaggata gcctggatag cttgtatgtc aacctgattc cggtttaatg a              1671
```

```
<210> SEQ ID NO 12
<211> LENGTH: 30
<212> TYPE: DNA
<213> ORGANISM: Artificial sequence
<220> FEATURE:
<223> OTHER INFORMATION: Primer

<400> SEQUENCE: 12
ctagccatgg cttcagaaaa agaaattagg                                         30

<210> SEQ ID NO 13
<211> LENGTH: 40
<212> TYPE: DNA
<213> ORGANISM: Artificial sequence
<220> FEATURE:
<223> OTHER INFORMATION: Primer

<400> SEQUENCE: 13
ccggaattcc tatttgcttc tcttgtaaac tttgttcaag                              40

<210> SEQ ID NO 14
<211> LENGTH: 42
<212> TYPE: DNA
<213> ORGANISM: Artificial sequence
<220> FEATURE:
<223> OTHER INFORMATION: Primer

<400> SEQUENCE: 14
aaggagatat acatatgaca aaaaaagttg gtgtcggtca gg                           42

<210> SEQ ID NO 15
<211> LENGTH: 43
<212> TYPE: DNA
```

-continued

```
<213> ORGANISM: Artificial sequence
<220> FEATURE:
<223> OTHER INFORMATION: Primer

<400> SEQUENCE: 15
ctttaccaga ctcgagttac gcctttttca tctgatcctt tgc                         43

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
atggctacta cggctgcttt ttgtc                                             25

<210> SEQ ID NO 17
<211> LENGTH: 28
<212> TYPE: DNA
<213> ORGANISM: Artificial sequence
<220> FEATURE:
<223> OTHER INFORMATION: Primer

<400> SEQUENCE: 17
tcattaaacc ggaatcaggt tgacatac                                          28
```

METHOD FOR PRODUCING (+)-ZIZAENE

This application is a 371 filing of International Patent Application PCT/IB2010/052103 filed May 12, 2010.

TECHNICAL FIELD

The present invention provides a method of producing (+)-zizaene, said method comprising contacting at least one polypeptide with farnesyl pyrophosphate (FPP). In particular, said method may be carried out in vitro or in vivo to produce (+)-zizaene, a compound which can be used as precursor for diverse compounds useful in the fields of perfumery and flavoring. The present invention also provides the amino acid sequence of a polypeptide useful in the method of the invention. A nucleic acid encoding the polypeptide of the invention and an expression vector containing said nucleic acid are also part of the present invention. A non-human host organism or a cell transformed to be used in the method of producing (+)-zizaene is also an object of the present invention.

PRIOR ART

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Over 300 sesquiterpene hydrocarbons and 3000 sesquiterpenoids have been identified and many new structures are identified each year. Plant extracts obtained by different means such as steam distillation or solvent extraction are used as source of terpenes. Terpene molecules are often used as such, but in some cases chemical reactions are used to transform the terpenes into other high value molecules.

Biosynthetic production of terpenes involves enzymes called terpene synthases. There is virtually an infinity of sesquiterpene synthases present in the plant kingdom, all using the same substrate (farnesyl pyrophosphate, FPP) but having different product profiles. Genes and cDNAs encoding sesquiterpene synthases have been cloned and the corresponding recombinant enzymes characterized. The biosynthesis of terpenes in plants and other organisms has been extensively studied and is not further detailed in here.

Generally, the price and availability of plant natural extracts are dependent on the abundance, oil yield and geographical origin of the plants. In addition, the availability and quality of natural extracts is very much dependent on climate and other local conditions leading to variability from year to year, rendering the use of such ingredients in high quality perfumery very difficult or even impossible some years.

Vetiver oil is one of these natural extracts. It is a relatively expensive perfuming ingredient, which consists of a complex mixture of sesquiterpene alcohols, aldehydes and acids having a complex olfactory profile. The individual constituents of vetiver oil could also be useful as perfuming ingredients but their purification from the oil is not feasible at large scale.

A plant-independent method for producing the vetiver oil constituents would therefore be very desirable but a cost-effective chemical synthesis of such compounds is so far not available.

(+)-Zizaene is a naturally occurring sesquiterpene molecule. It can be used as precursor for various compounds which are useful in the field of perfumery and flavoring, in particular for constituents of vetiver oil like khusimol, zizaen-12-al and khuzenic acid. A biochemical pathway leading to the synthesis of (+)-zizaene would therefore be of great interest.

Analysis of the composition of vetiver oil showed that zizaene derivatives are major constituents of this oil and contribute to the vetiver odor. See for example Weyerstahl et al (2000), Flav. Fragr. J., 15, 395-412. Nevertheless, this document does not provide or even suggest an amino acid or nucleotide sequence leading to the production of (+)-zizaene.

The biosynthesis of vetiver oil in vetiver roots has been investigated in Del Giudice et al (2008), *The microbial community of Vetiver root and its involvement into essential oil biogenesis*, Environ. Microbiol., 10(10), 2824-2841. This publication describes the production of sesquiterpenes by microorganisms isolated from vetiver roots and supports the idea of the microorganisms implicated in the biosynthesis of vetiver sesquiterpenes. Our results are in opposition to the suggestions made in this article because we show that zizaene is produced by a sesquiterpene synthase expressed by the vetiver roots themselves and not by the microbial community.

A sesquiterpene synthase capable of synthesizing a precursor of the vetiver oil constituents, in particular (+)-zizaene, has never been disclosed in the prior art.

The percentage of identity between the known sesquiterpene synthases and the polypeptide of the invention is very low. The closest protein sequence to the (+)-zizaene synthase of the invention is a putative terpene synthase from *Zea mays* (NCBI access No ACG24265) which shares 56% amino acid sequence identity with the (+)-zizaene synthase of the invention. The products obtained with this putative terpene synthase have not been identified. The closest fully characterized synthase is a (E)-beta-caryophyllene synthase from *Zea mays* (NCBI access No ABY79212), which is only 51% identical to the synthase of the invention.

In addition to the difference between the sequences themselves, it also has to be pointed out that the structure and the properties of the products synthesized by the above-mentioned enzyme are very different from those of (+)-zizaene. In particular (E)-beta-caryophyllene is not suitable as a precursor for the production of vetiver oil constituents.

Despite extensive studies of terpene cyclization, the isolation and characterization of the terpene synthases is still difficult, particularly in plants, due to their low abundance, their often transient expression patterns, and the complexity of purifying them from the mixtures of resins and phenolic compounds in tissues where they are expressed.

It is an objective of the present invention to provide methods for making (+)-zizaene in an economic way, as indicated above. Accordingly, the present invention has the objective to produce (+)-zizaene while having little waste, a more energy and resource efficient process and while reducing dependency on fossil fuels. It is a further objective to provide enzymes capable of synthesizing (+)-zizaene, which is useful as precursor for perfumery and/or aroma ingredients.

ABBREVIATIONS USED bp base pair
kb kilo base
BSA bovine serum albumin
cDNA complementary DNA
CTAB cethyltrimethylammonium bromide
DMAPP dimethylallyl diphosphate DNA deoxyribonucleic acid
dATP deoxy adenosine triphosphate
dNTP deoxy nucleotide triphosphate
DTT dithiothreitol
EDTA ethylenediaminetetraacetic acid
FPP farnesyl pyrophosphate
GC gaseous chromatograph
idi isopentenyl diphosphate isomerase
IPP isopentenyl diphosphate
IPTG isopropyl-D-thiogalacto-pyranoside
LB lysogeny broth
MOPSO 3-(N-morpholino)-2-hydroxypropanesulfonic acid
MS mass spectrometer
mvaK1 mevalonate kinase
mvaK2 mevalonate diphosphate kinase
PCR polymerase chain reaction
PVP polyvinylpyrrolidone
RMCE recombinase-mediated cassette exchange
3'-/5'-RACE 3' and 5' rapid amplification of cDNA ends
RNA ribonucleic acid
mRNA messenger ribonucleic acid
TE tris and EDTA
YNB yeast nitrogen base

DESCRIPTION OF THE INVENTION

The present invention provides a method to biosynthetically produce (+)-zizaene in an economic, reliable and reproducible way.

A "sesquiterpene synthase" or a "polypeptide having a sesquiterpene synthase activity" is intended here as a polypeptide capable of catalyzing the synthesis of a sesquiterpene molecule or of a mixture of sesquiterpene molecules from the acyclic terpene precursor FPP.

As a "(+)-zizaene synthase" or as a "polypeptide having a (+)-zizaene synthase activity", we mean here a polypeptide capable of catalyzing the synthesis of (+)-zizaene starting from FPP. (+)-Zizaene may be the only product or may be part of a mixture of sesquiterpenes.

The ability of a polypeptide to catalyze the synthesis of a particular sesquiterpene (for example (+)-zizaene) can be simply confirmed by performing the enzyme assay as detailed in Example 3.

According to the present invention, polypeptides are also meant to include truncated polypeptides provided that they keep their sesquiterpene synthase activity as defined in any of the above embodiments and that they share at least the defined percentage of identity with the corresponding fragment of SEQ ID NO:1.

As intended herein below, "a nucleotide sequence obtained by modifying SEQ ID NO:2, SEQ ID NO:11 or the complement thereof" encompasses any sequence that has been obtained by changing the sequence of SEQ ID NO:2, of SEQ ID NO:11 or of the complement of one of these two sequences using any method known in the art, for example by introducing any type of mutations such as deletion, insertion or substitution mutations. Examples of such methods are cited in the part of the description relative to the variant polypeptides and the methods to prepare them.

The percentage of identity between two peptidic or nucleotidic sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity.

Alignment for the purpose of determining the percentage of amino acid or nucleic acid sequence identity can be achieved in various ways using computer programs and for instance publicly available computer programs available on the worldwide web. Preferably, the BLAST program (Tatiana et al, *FEMS Microbiol Lett.*, 1999, 174:247-250, 1999) set to the default parameters, available from the National Center for Biotechnology Information (NCBI) at http://www.ncbi.nlm.nih.gov/BLAST/bl2seq/wblast2.cgi, can be used to obtain an optimal alignment of peptidic or nucleotidic sequences and to calculate the percentage of sequence identity.

One object of the present invention is therefore a method for producing (+)-zizaene comprising
 a) contacting FPP with at least one polypeptide having a (+)-zizaene synthase activity and comprising an amino acid sequence at least 50% identical to SEQ ID NO:1;
 b) optionally, isolating the (+)-zizaene produced in step a).

According to a preferred embodiment, the method is a method for producing (+)-zizaene as a major product. According to an even more preferred embodiment, (+)-zizaene represents at least 50%, preferably at least 60%, preferably at least 80%, preferably at least 90% of the product produced by the method of the invention.

The method can be carried out in vitro as well as in vivo, as will be explained in details further on.

The polypeptide to be contacted with FPP in vitro can be obtained by extraction from any organism expressing it, using standard protein or enzyme extraction technologies. If the host organism is an unicellular organism or cell releasing the polypeptide of the invention into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and further extraction of the polypeptide from the cell lysate.

The polypeptide having a (+)-zizaene synthase activity, either in an isolated form or together with other proteins, for example in a crude protein extract obtained from cultured cells or microorganisms, may then be suspended in a buffer solution at optimal pH. If adequate, salts, BSA and other kinds of enzymatic co-factors, may be added in order to optimize enzyme activity. Appropriate conditions are described in more details in the Examples further on.

The precursor FPP may then be added to the suspension or solution, which is then incubated at optimal temperature, for example between 15 and 40° C., preferably between 25 and 35° C., more preferably at 30° C. After incubation, the (+)-zizaene produced may be isolated from the incubated solution by standard isolation procedures, such as solvent extraction and distillation, optionally after removal of polypeptides from the solution.

According to another preferred embodiment, the method of any of the above-described embodiments is carried out in vivo. In this case, step a) comprises cultivating a non-human host organism or cell capable of producing FPP and transformed to express at least one polypeptide comprising an amino acid sequence at least 50% identical to SEQ ID NO:1 and having a (+)-zizaene synthase activity, under conditions conducive to the production of (+)-zizaene.

According to a more preferred embodiment, the method further comprises, prior to step a), transforming a non human organism or cell capable of producing FPP with at least one nucleic acid encoding a polypeptide comprising an amino acid sequence at least 50% identical to SEQ ID NO:1 and having a (+)-zizaene synthase activity, so that said organism expresses said polypeptide.

These embodiments of the invention are particularly advantageous since it is possible to carry out the method in vivo without previously isolating the polypeptide. The reaction occurs directly within the organism or cell transformed to express said polypeptide.

According to a particular embodiment of the invention, the at least one nucleic acid encoding the (+)-zizaene synthase comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, SEQ ID NO:11 or the complement thereof. According to a more preferred embodiment, said nucleic acid comprises the nucleotide sequence SEQ ID NO:2, SEQ ID NO:11 or the complement thereof. In an even more preferred embodiment, said nucleic acid consists of SEQ ID NO:2, SEQ ID NO:11 or the complement thereof.

According to a more preferred embodiment the at least one nucleic acid used in any of the above embodiments comprises a nucleotide sequence that has been obtained by modifying SEQ ID NO:2, SEQ ID NO:11 or the complement thereof. According to an even more preferred embodiment, said at least one nucleic acid consists of a nucleotide sequence that has been obtained by modifying SEQ ID NO:2, SEQ ID NO:11 or the complement thereof.

According to another embodiment, the at least one nucleic acid is isolated from *Vetiveria zizanoides.*

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells as specific objects of the present invention and in the examples.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art. Such methods can for example be found in the literature, for example in the following publications Martin, V. J., Pitera, D. J., Withers, S. T., Newman, J. D., and Keasling, J. D. *Nat Biotechnol.,* 2003, 21(7), 796-802 (transformation of *E. coli*); Wu, S., Schalk, M., Clark, A., Miles, R. B., Coates, R., and Chappell, J., *Nat Biotechnol.,* 2006, 24(11), 1441-1447 (transformation of plants); Takahashi, S., Yeo, Y., Greenhagen, B. T., McMullin, T., Song, L., Maurina-Brunker, J., Rosson, R., Noel, J., Chappell, J, *Biotechnology and Bioengineering,* 2007, 97(1), 170-181 (transformation of yeast).

To carry out the invention in vivo, the host organism or cell is cultivated under conditions conducive to the production of (+)-zizaene. Accordingly, if the host is a transgenic plant, optimal growth conditions are provided, such as optimal light, water and nutrient conditions, for example. If the host is a unicellular organism, conditions conducive to the production of (+)-zizaene may comprise addition of suitable cofactors to the culture medium of the host. In addition, a culture medium may be selected, so as to maximize (+)-zizaene synthesis. Optimal culture conditions are described in a more detailed manner in the following Examples.

Non-human host organisms suitable to carry out the method of the invention in vivo may be any non-human multicellular or unicellular organisms. In a preferred embodiment, the non-human host organism used to carry out the invention in vivo is a plant, a prokaryote or a fungus. Any plant, prokaryote or fungus can be used. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum.*

In a more preferred embodiment the non-human host organism used to carry out the method of the invention in vivo is a microorganism. Any microorganism can be used but according to an even more preferred embodiment said microorganism is a bacteria or yeast. Most preferably, said bacteria is *E. coli* and said yeast is *Saccharomyces cerevisiae.*

Some of these organisms do not produce FPP naturally. To be suitable to carry out the method of the invention, these organisms have to be transformed to produce said precursor. They can be so transformed either before the modification with the nucleic acid described according to any of the above embodiments or simultaneously, as explained above.

Isolated higher eukaryotic cells can also be used, instead of complete organisms, as hosts to carry out the method of the invention in vivo. Suitable eukaryotic cells may be any non-human cell, but are preferably plant or fungal cells.

According to a preferred embodiment, the at least one polypeptide having a (+)-zizaene synthase activity used in any of the above-described embodiments or encoded by the nucleic acid used in any of the above-described embodiments comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, said polypeptide comprises the amino acid sequence SEQ ID NO:1. In an even more preferred embodiment, said polypeptide consists of SEQ ID NO:1.

According to another preferred embodiment, the at least one polypeptide having a (+)-zizaene synthase activity used in any of the above-described embodiments or encoded by the nucleic acid used in any of the above-described embodiments comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2, SEQ ID NO:11 or the complement thereof. According to a more preferred embodiment, the at least one polypeptide having a (+)-zizaene synthase activity used in any of the above-described embodiments or encoded by the nucleic acid used in any of the above-described embodiments consists of an amino acid sequence that is a variant of SEQ ID NO:1 obtained by genetic engineering, i.e. an amino acid sequence encoded by a nucleotide sequence that has been obtained by modifying SEQ ID NO:2, SEQ ID NO:11 or the complement thereof.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention. For example, as detailed in Example 4 below, SEQ ID NO:11 is a variant of SEQ ID NO:2, obtained by artificial mutation of SEQ ID NO:2, leading to a nucleotide sequence which is optimized for expression in *E. coli* and which encodes the same (+)-zizaene synthase as SEQ ID NO:2 (i.e. SEQ ID NO:1). The sequences SEQ ID NO:2 and SEQ ID NO:11 are 76% identical.

Polypeptide variants resulting from a fusion of additional peptide sequences at the amino and carboxyl terminal ends can also be used in the methods of the invention. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, the present invention encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of the invention.

According to another embodiment, the at least one polypeptide having a (+)-zizaene synthase activity used in any of the above-described embodiments or encoded by the nucleic acid used in any of the above-described embodiments is isolated from *Vetiveria zizanoides*.

An important tool to carry out the method of the invention is the polypeptide itself. A polypeptide having a (+)-zizaene synthase activity and comprising an amino acid sequence at least 50% identical to SEQ ID NO:1 is therefore another object of the present invention.

According to a preferred embodiment, the polypeptide is capable of producing (+)-zizaene as a major product. According to an even more preferred embodiment, it is capable of producing a mixture of sesquiterpenes wherein (+)-zizaene represents at least 60%, preferably at least 80%, preferably at least 90% of the sesquiterpenes produced.

According to a more preferred embodiment, the polypeptide has a (+)-zizaene synthase activity.

According to a preferred embodiment, the polypeptide comprises an amino acid sequence at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:1. According to a more preferred embodiment, the polypeptide comprises the amino acid sequence SEQ ID NO:1. According to an even more preferred embodiment, the polypeptide consists of SEQ ID NO:1.

According to another preferred embodiment, the polypeptide comprises an amino acid sequence that is a variant of SEQ ID NO:1 obtained by genetic engineering. In other terms, said polypeptide comprises an amino acid sequence encoded by a nucleotide sequence that has been obtained by modifying SEQ ID NO:2, SEQ ID NO:11 or the complement thereof. According to a more preferred embodiment, the polypeptide having a (+)-zizaene synthase activity consists of an amino acid sequence that is a variant of SEQ ID NO:1 obtained by genetic engineering, i.e. an amino acid sequence encoded by a nucleotide sequence that has been obtained by modifying SEQ ID NO:2, SEQ ID NO:11 or the complement thereof.

According to another embodiment, the polypeptide is isolated form *Vetiveria zizanoides*.

As used herein, the polypeptide is intended as a polypeptide or peptide fragment that encompasses the amino acid sequences identified herein, as well as truncated or variant polypeptides, provided that they keep their activity as defined above and that they share at least the defined percentage of identity with the corresponding fragment of SEQ ID NO:1.

Examples of variant polypeptides are naturally occurring proteins that result from alternate mRNA splicing events or form proteolytic cleavage of the polypeptides described herein. Variations attributable to proteolysis include, for example, differences in the N- or C-termini upon expression in different types of host cells, due to proteolytic removal of one or more terminal amino acids from the polypeptides of the invention. Polypeptides encoded by a nucleic acid obtained by natural or artificial mutation of a nucleic acid of the invention, as described thereafter, are also encompassed by the invention. For example, as detailed in Example 4 below, SEQ ID NO:11 is a variant of SEQ ID NO:2, obtained by artificial mutation of SEQ ID NO:2, leading to a nucleotide sequence which is optimized for expression in *E. coli* and which encodes the same (+)-zizaene synthase as SEQ ID NO:2 (i.e. SEQ ID NO:1). The sequences SEQ ID NO:2 and SEQ ID NO:11 are 76% identical.

Polypeptide variants resulting from a fusion of additional peptide sequences at the amino and carboxyl terminal ends are also encompassed by the polypeptides of the invention. In particular such a fusion can enhance expression of the polypeptides, be useful in the purification of the protein or improve the enzymatic activity of the polypeptide in a desired environment or expression system. Such additional peptide sequences may be a signal peptide, for example. Accordingly, the present invention encompasses variants of the polypeptides of the invention, such as those obtained by fusion with other oligo- or polypeptides and/or those which are linked to signal peptides. Polypeptides resulting from a fusion with another functional protein, such as another protein from the terpene biosynthesis pathway, are also encompassed by the polypeptides of the invention.

As mentioned above, the nucleic acid encoding the polypeptide of the invention is a useful tool to modify non-human host organisms or cells intended to be used when the method is carried out in vivo.

A nucleic acid encoding a polypeptide according to any of the above-described embodiments is therefore also an object of the present invention.

According to a preferred embodiment, the nucleic acid comprises a nucleotide sequence at least 50%, preferably at least 55%, preferably at least 60%, preferably at least 65%, preferably at least 70%, preferably at least 75%, preferably at least 80%, preferably at least 85%, preferably at least 90%, more preferably at least 95% and even more preferably at least 98% identical to SEQ ID NO:2, SEQ ID NO:11 or the complement thereof. According to a more preferred embodiment, the nucleic acid comprises the nucleotide sequence SEQ ID NO:2, SEQ ID NO:11 or the complement thereof. According to an even more preferred embodiment, the nucleic acid consists of SEQ ID NO:2, SEQ ID NO:11 or the complement thereof.

According to another embodiment, the nucleic acid is isolated from *Vetiveria zizanoides*.

The nucleic acid of the invention can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of the invention also encompass certain isolated nucleotide sequences including those that are substantially free from contaminating endogenous material. The nucleic acid of the invention may be truncated, provided that it encodes a polypeptide encompassed by the present invention, as described above.

According to a more preferred embodiment, the at least one nucleic acid according to any of the above embodiments comprises a nucleotide sequence that has been obtained by modifying SEQ ID NO:2, SEQ ID NO:11 or the complement thereof. Preferably said nucleic acid consists of a nucleotide sequence that has been obtained by modifying SEQ ID NO:2, SEQ ID NO:11 or the complement thereof.

The nucleic acids comprising a sequence obtained by mutation of SEQ ID NO:2, SEQ ID NO:11 or the complement thereof are encompassed by the invention, provided that the sequences they comprise share at least the defined percentage of identity with the corresponding fragments of SEQ ID NO:2, SEQ ID NO:11 or the complement thereof and provided that they encode a polypeptide having a (+)-zizaene synthase activity, as defined in any of the above embodiments. Mutations may be any kind of mutations of these nucleic acids, such as point mutations, deletion mutations, insertion mutations and/or frame shift mutations. A variant nucleic acid may be prepared in order to adapt its nucleotide sequence to a specific expression system. For example, bacterial expression systems are known to more efficiently express polypeptides if amino acids are encoded by a preferred codon. Due to the degeneracy of the genetic code, wherein more than one codon can encode the same amino acid, multiple DNA sequences can code for the same polypeptide, all these DNA sequences being encompassed by the invention.

Another important tool for transforming host organisms or cells suitable to carry out the method of the invention in vivo is an expression vector comprising a nucleic acid according to any embodiment of the invention. Such a vector is therefore also an object of the present invention.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of the invention operably linked to at least one regulatory sequence, which controls initiation and/or termination of the transcription and/or translation, such as a transcriptional promoter, operator or enhancer, or an mRNA ribosomal binding site and, optionally, including at least one selection marker. Nucleotide sequences are "operably linked" when the regulatory sequence functionally relates to the nucleic acid of the invention.

The expression vectors of the present invention may be used in the methods for preparing a genetically transformed host organism and/or cell, in host organisms and/or cells harboring the nucleic acids of the invention and in the methods for producing or making polypeptides having a (+)-zizaene synthase activity, as disclosed further below.

Recombinant non-human host organisms and cells transformed to harbor at least one nucleic acid of the invention so that it heterologously expresses or over-expresses at least one polypeptide of the invention are also very useful tools to carry out the method of the invention. Such non-human host organisms and cells are therefore another object of the present invention.

A nucleic acid according to any of the above-described embodiments can be used to transform the non-human host organisms and cells and the expressed polypeptide can be any of the above-described polypeptides.

Non-human host organisms of the invention may be any non-human multicellular or unicellular organisms. In a preferred embodiment, the non-human host organism is a plant, a prokaryote or a fungus. Any plant, prokaryote or fungus is suitable to be transformed according to the present invention. Particularly useful plants are those that naturally produce high amounts of terpenes. In a more preferred embodiment, the plant is selected from the family of Solanaceae, Poaceae, Brassicaceae, Fabaceae, Malvaceae, Asteraceae or Lamiaceae. For example, the plant is selected from the genera *Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum*.

In a more preferred embodiment the non-human host organism is a microorganism. Any microorganism is suitable for the present invention, but according to an even more preferred embodiment said microorganism is a bacteria or yeast. Most preferably, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Preferred higher eukaryotic cells are plant cells or fungal cells.

The term "transformed" refers to the fact that the host was subjected to genetic engineering to comprise one, two or more copies of each of the nucleic acids required in any of the above-described embodiment. Preferably the term "transformed" relates to hosts heterologously expressing the polypeptides encoded by the nucleic acid with which they are transformed, as well as over-expressing said polypeptides. Accordingly, in an embodiment, the present invention provides a transformed organism, in which the polypeptides are expressed in higher quantity than in the same organism not so transformed.

There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., *Cloning Vectors: A Laboratory Manual,* 1985, Elsevier, New York and Sambrook et al., *Molecular Cloning: A Laboratory Manual*, 2nd edition, 1989, Cold Spring Harbor Laboratory Press. Cloning and expression vectors for higher plants and/or plant cells in particular are available to the skilled person. See for example Schardl et al. *Gene* 61: 1-11, 1987.

Methods for transforming host organisms or cells to harbor transgenic nucleic acids are familiar to the skilled person. For the creation of transgenic plants, for example, current methods include: electroporation of plant protoplasts, liposome-mediated transformation, agrobacterium-mediated transformation, polyethylene-glycol-mediated transformation, particle bombardment, microinjection of plant cells, and transformation using viruses.

In one embodiment, transformed DNA is integrated into a chromosome of a non-human host organism and/or cell such that a stable recombinant system results. Any chromosomal integration method known in the art may be used in the practice of the invention, including but not limited to recombinase-mediated cassette exchange (RMCE), viral site-specific chromosomal insertion, adenovirus and pronuclear injection.

In order to carry out the method for producing (+)-zizaene in vitro, as exposed herein above, it is very advantageous to provide a method of making at least one polypeptide having a (+)-zizaene synthase activity as described in any embodiment of the invention. Therefore, the invention provides a method for producing at least one polypeptide according to any embodiment of the invention comprising
  a) culturing a non-human host organism or cell according to any embodiment of the invention;
  b) isolating the polypeptide from the non-human host organism or cell cultured in step a).

According to a preferred embodiment, said method further comprises, prior to step a), transforming a non-human host organism or cell with at least one nucleic acid according to any embodiment of the invention, so that said organism expresses the polypeptide encoded by said nucleic acid.

A nucleic acid according to any of the above-described embodiments can be used.

Transforming and culturing of the non-human host organism or cell can be carried out as described above for the method of producing (+)-zizaene in vivo. Step b) may be performed using any technique well known in the art to isolate a particular polypeptide from an organism or cell.

A "polypeptide variant" as referred to herein means a polypeptide having a (+)-zizaene synthase activity and being substantially homologous to the polypeptide according to any of the above embodiments, but having an amino acid sequence different from that encoded by any of the nucleic acid sequences of the invention because of one or more deletions, insertions or substitutions.

Variants can comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. See Zubay, *Biochemistry*, 1983, Addison-Wesley Pub. Co. The effects of such substitutions can be calculated using substitution score matrices such a PAM-120, PAM-200, and PAM-250 as discussed in Altschul, *J. Mol. Biol.*, 1991, 219, 555-565. Other such conservative substitutions, for example substitutions of entire regions having similar hydrophobicity characteristics, are well known.

Naturally occurring peptide variants are also encompassed by the invention. Examples of such variants are proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides encoded by the sequences of the invention.

Variants of the polypeptides of the invention may be used to attain for example desired enhanced or reduced enzymatic activity, modified regiochemistry or stereochemistry, or altered substrate utilization or product distribution, increased affinity for the substrate, improved specificity for the production of one or more desired compounds, increased velocity of the enzyme reaction, higher activity or stability in a specific environment (pH, temperature, solvent, etc), or improved expression level in a desired expression system. A variant or site directed mutant may be made by any method known in the art. Variants and derivatives of native polypeptides can be obtained by isolating naturally-occurring variants, or the nucleotide sequence of variants, of other or same plant lines or species, or by artificially programming mutations of nucleotide sequences coding for the polypeptides of the invention. Alterations of the native amino acid sequence can be accomplished by any of a number of conventional methods.

Polypeptide variants resulting from a fusion of additional peptide sequences at the amino and carboxyl terminal ends of the polypeptides of the invention can be used to enhance expression of the polypeptides, be useful in the purification of the protein or improve the enzymatic activity of the polypeptide in a desired environment or expression system. Such additional peptide sequences may be signal peptides, for example. Accordingly, the present invention encompasses variants of the polypeptides of the invention, such as those obtained by fusion with other oligo- or polypeptides and/or those which are linked to signal peptides. Fusion polypeptides encompassed by the invention also comprise fusion polypeptides resulting from a fusion of other functional proteins, such as other proteins from the terpene biosynthesis pathway.

Therefore, in an embodiment, the present invention provides a method for preparing a variant polypeptide having a (+)-zizaene synthase activity, as described in any of the above embodiments, and comprising the steps of:
  (a) selecting a nucleic acid according to any of the embodiments exposed above;
  (b) modifying the selected nucleic acid to obtain at least one mutant nucleic acid;
  (c) transforming host cells or unicellular organisms with the mutant nucleic acid sequence to express a polypeptide encoded by the mutant nucleic acid sequence;
  (d) screening the polypeptide for at least one modified property; and,
  (e) optionally, if the polypeptide has no desired variant (+)-zizaene synthase activity, repeating the process steps (a) to (d) until a polypeptide with a desired variant (+)-zizaene synthase activity is obtained;
  (f) optionally, if a polypeptide having a desired variant (+)-zizaene synthase activity was identified in step (d), isolating the corresponding mutant nucleic acid obtained in step (c).

According to a preferred embodiment, the variant polypeptide prepared is capable of producing (+)-zizaene as a major product. According to an even more preferred embodiment, it is capable of producing a mixture of sesquiterpenes wherein (+)-zizaene represents at least 60%, preferably at least 80%, preferably at least 90% of the sesquiterpenes produced.

In step (b), a large number of mutant nucleic acid sequences may be created, for example by random mutagenesis, site-specific mutagenesis, or DNA shuffling. The detailed procedures of gene shuffling are found in Stemmer, DNA shuffling by random fragmentation and reassembly: in vitro recombination for molecular evolution. Proc Natl Acad Sci USA., 1994, 91(22): 10747-1075. In short, DNA shuffling refers to a process of random recombination of known sequences in vitro, involving at least two nucleic acids selected for recombination. For example mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered gene wherein predetermined codons can be altered by substitution, deletion or insertion.

Accordingly, the polypeptide comprising SEQ ID NO:1 may be recombined with any other sesquiterpene synthase encoding nucleic acids, for example isolated from an organism other than Veriveria zizanoides. Thus, mutant nucleic acids may be obtained and separated, which may be used for transforming a host cell according to standard procedures, for example such as disclosed in the present examples.

In step (d), the polypeptide obtained in step (c) is screened for at least one modified property, for example a desired modified enzymatic activity. Examples of desired enzymatic activities, for which an expressed polypeptide may be screened, include enhanced or reduced enzymatic activity, as measured by $K_M$ or $V_{max}$ value, modified regio-chemistry or stereochemistry and altered substrate utilization or product distribution. The screening of enzymatic activity can be performed according to procedures familiar to the skilled person and those disclosed in the present examples.

Step (e) provides for repetition of process steps (a)-(d), which may preferably be performed in parallel. Accordingly, by creating a significant number of mutant nucleic acids, many host cells may be transformed with different mutant nucleic acids at the same time, allowing for the subsequent screening of an elevated number of polypeptides. The chances of obtaining a desired variant polypeptide may thus be increased at the discretion of the skilled person.

All the publications mentioned in this application are incorporated by reference to disclose and describe the methods and/or materials in connection with which the publications are cited.

SPECIFIC EMBODIMENTS OF THE INVENTION OR EXAMPLES

Figure 1:
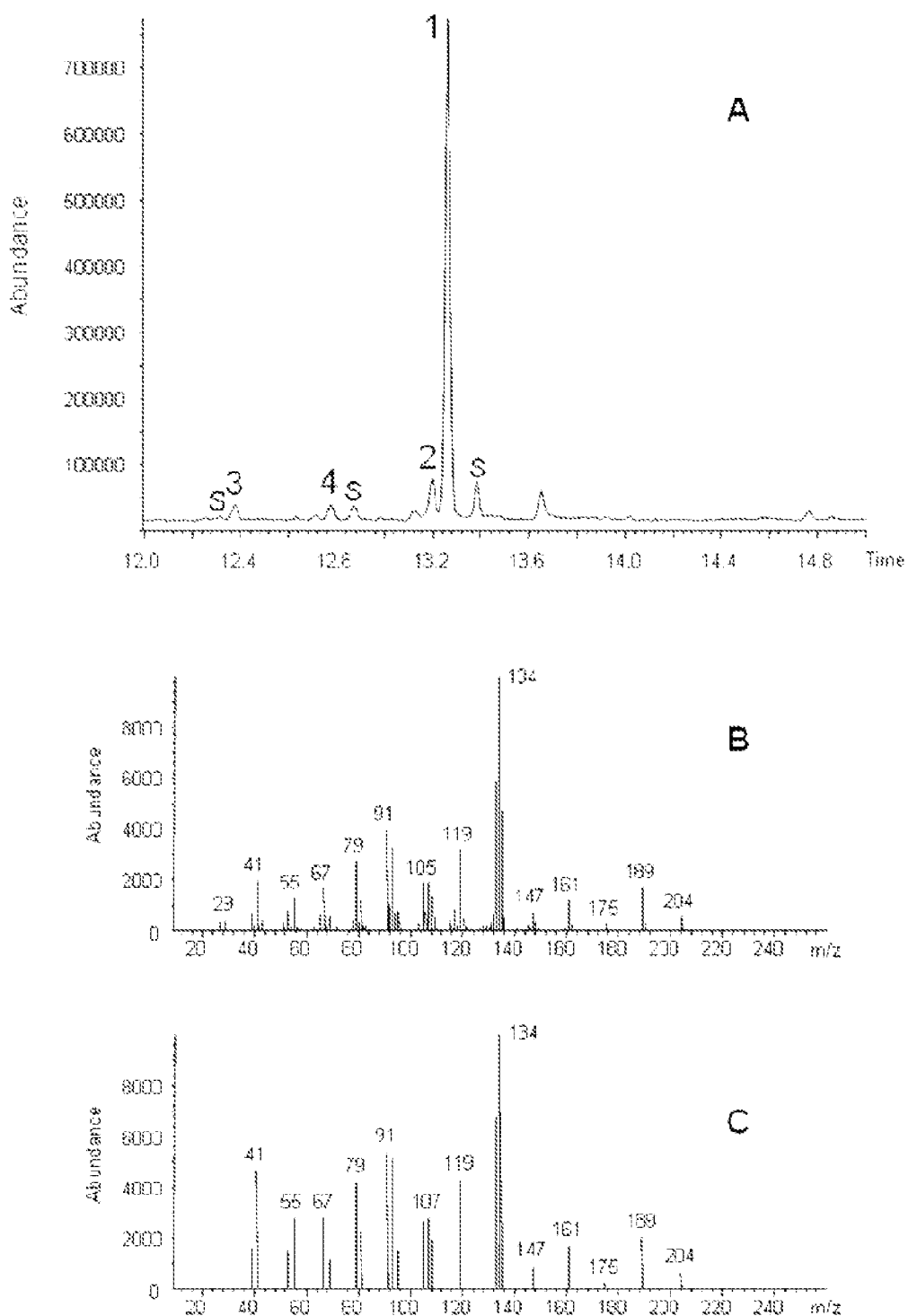
FIG. 1: GC-MS analysis of sesquiterpenes produced by the Vetiveria zizanoides (+)-zizaene synthase (VzZS). A, total ion chromatogram. B, mass spectrum of the major peak (1). C, mass spectrum of an authentic (+)-zizaene standard. Peak 1 was identified as the (+)-zizaene. Peaks 2, 3 and 4 were identified as prezizaene, α-funebrene and β-funebrene respectively. The peaks marked with S were unidentified sesquiterpene compounds.
Figure 2:
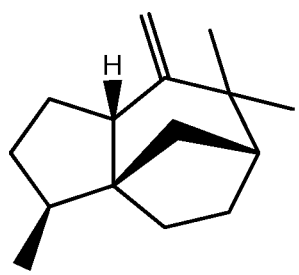
FIG. 2: Structure of the major sesquiterpene compounds produced by the Vetiveria zizanoides (+)-zizaene synthase (VzZS).
Figure 2:
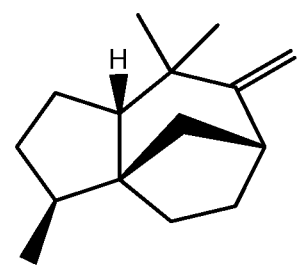
Figure 2:
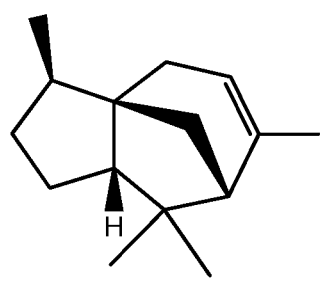
Figure 2:
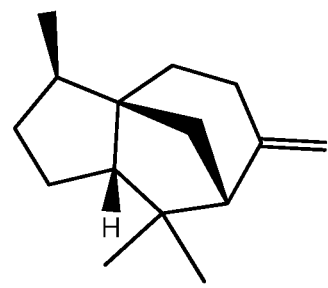

The invention will now be described in further detail by way of the following Examples.

Example 1

RNA Extraction and cDNA Library Construction

Vetiver (Vetiveria zizanoides) plants were obtained from a plant nursery (The Austral Plants Company, Les Avirons, The Reunion Island, France). The plants were cultivated in pots in a green house at the Lullier Agronomy research Station (Switzerland) and were propagated vegetatively by dividing six months to one-year-old clumps. For harvesting of the roots, the plants were removed from the pots and rinsed with tap water.

For preparation of the cDNA library, roots from several plants were combined: young plants (4 to 6 months after propagation), old plants with a well-developed dense root system (1 to 2 years after propagation) and young plants dried at room temperature for 24 to 36 hours after removing them from the pots. The roots were cut off from the aerial part of the plants and frozen in liquid nitrogen. They were first roughly chopped in liquid nitrogen using a Waring Blendor (Waring Laboratory, Torrington, USA) and then ground to a fine powder using a mortar and pestle. Total RNA was extracted following the procedure described in Kolosova et al (Kolosova, Miller, Ralph, Ellis, Douglas, Ritland and Bohlmann, Isolation of high-quality RNA from gymnosperm and angiosperm trees. J. Biotechniques, 36(5), 821-4, 2004) with the following modifications. A volume of 20 ml of extraction buffer was used for 2 grams of ground tissue and the extraction buffer was supplemented with 2% (w/v) of PVP (polyvinylpyrrolidone, Sigma-Aldrich). For the CTAB (cethyltrimethylammonium bromide, Sigma-Aldrich) extraction, the nucleic acid pellet was resuspended in 2 ml TE buffer (10 mM Tris-HCl, pH 8, 1 mM EDTA) and the extraction was performed with 2 ml of 5M NaCl and 1 ml 10% CTAB. For the isopropanol precipitation, the nucleic acid pellet was dissolved in 500 μl TE. The final RNA pellet was resuspended in 50 μl water.

A double stranded cDNA library was prepared using the SMART™ PCR cDNA Synthesis Kit (Clontech Laboratories, Mountain View, Calif.) according to the manufacturer's instructions and using SuperScript™ II RNAse H-reverse transcriptase (Invitrogen, Carlsbad, Calif.) for the reverse transcription step. An amount of 1 μg of vetiver underground tissue total RNA was used as template for the cDNA synthesis and 15 cycles were performed for the amplification procedure. The library was loaded on a 1% agarose gel and the fragments of sizes ranging from 1.3 to 3 Kb were eluted. For the sequencing 270 ng of this cDNA library was used.

Example 2 cDNA Library Sequencing and Amplification of a Sesquiterpene Synthase cDNA

The technology of massive parallel sequencing of small DNA fragments developed by Illumina (San Diego, Calif.) was used to sequence the whole cDNA library. The preparation of the DNA for sequencing, the sequencing and the assembling of the reads were performed by Fasteris SA (Plan-les-Ouates, Switzerland). The cDNA library was treated following the Genomic Sample Prep Kit (Illumina) and sequenced on the Genome Analyzer system (Illumina) A total 4.2 million of 35 bp reads were obtained (of which 3.6 million were unique sequences). These reads were assembled using EDENA 2.1.1, a software finding overlaps between the reads and assembling de novo contigs (Hernandez D., François P., Farinelli L., Østerås M., and Schrenzel J., De novo bacterial genome sequencing: Millions of very short reads assembled on a desktop computer. *Genome Res.* 18(5), 802-809, 2008). After eliminating contigs shorter than 100 bases, 4324 unique contigs were obtained with a maximum length of 1882 bp. Another assembling was performed using the Velvet 1.0 program (Zerbino and Birney (2008), Velvet: algorithms for de novo short read assembly using de Bruijn graphs. *Genome Res.* 18(5), 821-829), providing 9264 unique contigs of length between 100 and 2006 bases.

All the contigs generated were compared against a protein sequences database (containing a selection of 7000 plant protein sequences) using the Blastx algorithm (Altschul et al, J. Mol. Biol. 215, 403-410, 1990). The contigs showing significant sequence homology with plant sesquiterpene synthases were retained and the homology was further confirmed by performing, for each selected contig, a blast search against the NCBI non-redundant protein sequences (NCBI; http://www.ncbi.nlm.nih.gov). In this way, 15 contigs were confirmed as being fragments of sesquiterpene encoding cDNA.

One of the selected contigs (VzCtg306, SEQ ID NO:3) was of 1090 bp length and sequence comparisons with full-length terpene synthases showed that the 3' end and the 5' end were missing. Two forward primers (ctg306-3R1 (SEQ ID NO:4) and ctg306-3R2 (SEQ ID NO:5)) and two reverse primers (ctg306-5R1 (SEQ ID NO:6) and ctg306-5R2, (SEQ ID NO:7)) were designed from this sequence and used for the Rapid Amplification of cDNA Ends (RACE). The SMART™ RACE cDNA Amplification Kit (Clontech Laboratories, Mountain View, Calif.) was used with the PrimeScript reverse transcriptase (TaKaRa Bio, Shiga, Japan). Thus, a SMART™ 5' RACE-Ready cDNA and a SMART™ 3' RACE-Ready cDNA pool were prepared each from 1.2 µg vetiver root total RNA. For the 5' RACE, a first round PCR was performed with the UPM primers (Clontech Laboratories) and the ctg306-5R1 primer (SEQ ID NO:6) followed by a second round PCR with the NUP primer (Clontech Laboratories) and the ctg306-5R2 primer (SEQ ID NO:7). For the 3' RACE, a first round PCR was performed with the UPM primers (Clontech Laboratories) and the ctg306-3R1 (SEQ ID NO:4) primer followed by a second round PCR with the NUP primer (Clontech Laboratories) and the ctg306-3R2 primer (SEQ ID NO:5). The amplifications were performed in the conditions detailed in the manufacturer manual (Clontech).

The combination of the 5' and 3' RACE allowed the reconstitution of a 1925 bp cDNA (VzZS, SEQ ID NO:8) containing an open reading frame of 1668 bp (SEQ ID NO:2) encoding for a protein of 555 amino acids length (SEQ ID NO:1).

Example 3

Heterologous Expression and Enzyme Characterization

The full-length VzZS open reading frame (VzZS-ORF, SEQ ID NO:2) was amplified from the SMART™ 5' RACE-Ready cDNA pool using the primer ctg306-start (SEQ ID NO:9) and ctg306-stop (SEQ ID NO:10). The amplification of this cDNA for the expression constructs were performed using the Pfu DNA polymerase (Promega, Madison, Wis., USA), in a final volume of 50 µl containing 5 µl of Pfu DNA polymerase 10× buffer, 200 µM each dNTP, 0.4 µM each forward and reverse primer, 2.9 units Pfu DNA polymerase and 2.5 µl of the cDNA (prepared as described above). The thermal cycling conditions were as follows: 1.5 min at 95° C.; 30 cycles of 45 sec at 95° C., 30 sec 54° C. and 4 min at 72° C.; and 10 min at 72° C.

The PCR products were inserted into the pET101/D-TOPO vector using the Champion pET101 Directional TOPO Expression Kit (Invitrogen, Carlsbad, Calif.) following the manufacturer's instructions. Several clones were selected and the plasmid inserts sequenced to confirm that the sequence was identical to the sequence obtained by RACE.

The plasmid pET101-VzZS was used to transform B121 (DE3) *E. Coli* cells (Novagen, Madison, Wis.). Single colonies of transformed cells were used to inoculate 5 ml LB medium. After 5 to 6 hours incubation at 37° C., the cultures were transferred to a 20° C. incubator and left 1 hour for equilibration. Expression of the protein was then induced by the addition of 1 mM IPTG and the culture was incubated over-night at 20° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g) and the supernatants containing the soluble proteins were used for further experiments.

The crude *E coli* protein extracts containing the recombinant protein was used for the characterization of the enzymatic activities. Farnesyl-diphosphate (FPP) was synthesized as described by Keller, R. K., and Thompson, R., *J. Chromatogr.* 645(1), 161-167, 1993. The assays were performed in 1 to 4 mL of 50 mM MOPSO pH 7, 10% glycerol, 1 mM DTT, 10 mM $MgCl_2$ in the presence of 10 to 100 µM of substrate and 0.1 to 0.5 mg of crude protein. The tubes were incubated 12 to 24 hours at 30° C. and extracted twice with one volume of pentane. After concentration under a nitrogen flow, the extracts were analysed by GC and GC-MS and compared to extracts from assay with control proteins. The GC analysis was performed on an Agilent 6890 Series GC system equipped with a flame ionization detector using a 0.25 mm inner diameter by 30 m SPB-1 capillary column (Supelco, Bellefonte, Pa.). The carrier gas was He at a constant flow of 1 mL/min The initial oven temperature was 80° C. (1 min hold) followed by a gradient of 10° C./min to 300° C. The GC-MS analysis was performed in the same conditions and the spectra were recorded on an Agilent 5975 mass detector.

In these conditions, the recombinant protein encoded by the VzZS cDNA produced one major sesquiterpene representing 75% of the sesquiterpene mixture produced. This major product was identified as being (+)-zizaene by matching of the mass spectrum and retention index with authentic standards and published data (Joulain, D., and König, W. A., The Atlas of Spectral Data of Sesquiterpene Hydrocarbons, EB Verlag, Hamburg, 1998). The enzyme produces also 6.9% of prezizaene, 2.8% of α-funebrene, 2.7% of β-funebrene and at least 3 other sesquiterpenes at proportions between 0.85 and 8.7% (FIG. 2). Thus, the VzZS cDNA isolated from *Vetiveria zizanoides* encoded for a (+)-zizaene synthase (SEQ ID NO:1) producing the hydrocarbon precursor of the most abundant sesquiterpenes in vetiver roots (Khusimol, zizaen-12-al, khuzenic acid). The enzyme also produced as secondary products some of the precursors of minor constituents of vetiver roots.

Example 4

Use of the Recombinant VzZS Protein for In-Vivo Production of (+)-Zizaene in Bacteria For optimal expression of the VzZS in *E coli*, the DNA sequence of the ORF of the VzCtg306 cDNA was redesigned to take into account the host codon usage and other parameters influencing the stability of the mRNA and its translation. The optimized sequence (VzZS-opt, SEQ ID NO:11) was designed and synthesized with the MeI and KpnI restriction sites and the 3' and 5' ends (DNA 2.0, Menlo Park, Calif., USA) and subcloned into the pETDuet-1 plasmid (Novagene, Madison, Wis.) providing the plasmid pETDuet-VzZS-opt.

To evaluate the in-vivo production of (+)-zizaene, *E. coli* cells were transformed with the pETDuet-VzZS-opt plasmid and the production of sesquiterpenes from the endogenous FPP pool was evaluated. To increase the productivity of the cells, an FPP synthase and the genes encoding for a partial mevalonate pathway were also expressed in the same cells. These later genes were organized in a single operon and encoded for a mevalonate kinase (mvaK1), a phosphomevalonate kinase (mvaK2), a mevalonate diphosphate decarboxylase (MvaD) and an isopentenyl diphosphate isomerase (idi) and converted exogenous mevalonate to isopentenyl diphosphate (IPP) and dimethylallyl diphosphate (DMAPP), the two substrates of the FPP synthase.

The yeast FPP synthase gene was amplified from *S. cerevisiae* genomic DNA using the primers FPPy_NcoI (SEQ ID NO:12) and FPPy-Eco (SEQ ID NO:13). The genomic DNA was isolated from *S. cerevisiae* using the Qiagen RNA/DNA Maxi Kit (Qiagen AG, Basel, Switzerland). The PCR was performed with the Pfu DNA polymerase (Promega AG, Dubendorf, Switzerland) in a final volume of 50 µl containing 0.4 µl of each primer, 200 µM dNTPs, 0.5 µl DNA polymerase 5 µl *S. cerevisiae* genomic DNA. The PCR cycling condition were as follows: 90 sec at 95° C.; 28 cycles of 45 sec at 95° C., 30 sec at 54° C. and 4 min at 72° C.; 10 min at 72° C. The amplified DNA was ligated as NdeI-EcoRI fragment in the first multi cloning site (MCS1) of the pACYCDuet-1 plasmid (Novagen, Madison, Wis.) providing the plasmid pACYCDuet-FPPs harbouring the FPPs gene under the control of a T7 promoter.

An operon containing the genes encoding for mvaK1, mvaK2, MvaD and idi was amplified from genomic DNA of *Streptococcus pneumoniae* (ATCC BAA-334, LGC Standards, Molsheim, France) with the primers MVA-up1-start (SEQ ID NO:14) and MVA-up2-stop (SEQ ID NO:15). The PCR was performed using the PfuUltra™ II Fusion HS DNA polymerase (Stratagene, Agilent Technologies Inc., Santa Clara, Calif., USA). The composition of the PCR mix was according to the manufacturer instructions. The thermal cycling condition were 2 min at 95° C.; 30 cycles of 20 sec at 95° C., 20 sec at 58° C. and 90 sec at 72° C.; and 3 min at 72° C. The 3.8 Kb fragment was purified on an agarose gel and ligated using the In-Fusion™ Dry-Down PCR Cloning Kit (Clontech Laboratories) into the second MCS of the pACYCDuet-FPPs plasmid digested with NdeI and XhoI providing the plasmid pACYCDuet-4506. The sequences of the two inserts were fully sequenced to exclude any mutation.

Figure 3:
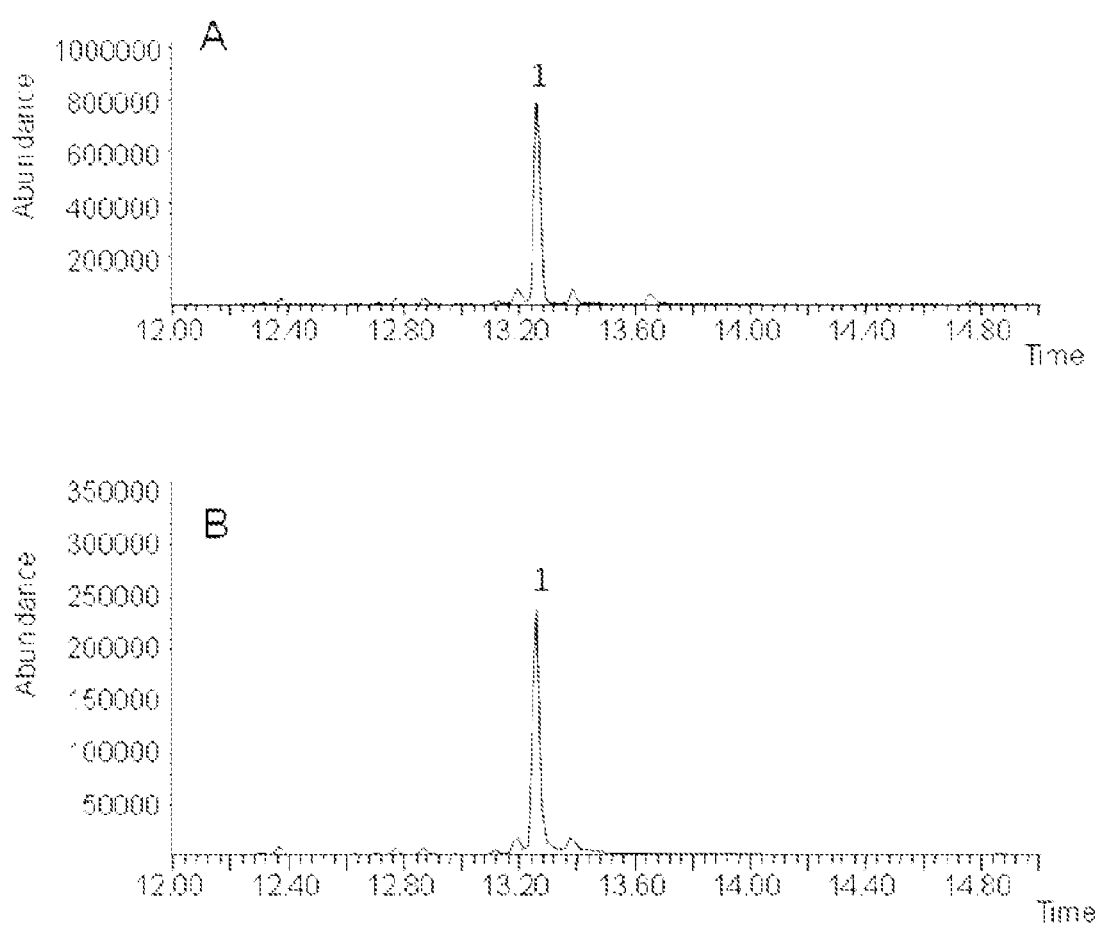
FIG. 3: Product profile obtained by in-vitro (A) and in-vivo (B) production of (+)-zizaene. The major peak in each analysis is (+)-zizaene.

BL21 Star™(DE3) *E. coli* cells (Invitrogen, Carlsbad, Calif.) were transformed with the plasmid pETDuet-VzZS-opt or co-transformed with the same plasmid and with the plasmid pACYCDuet-4506. Transformed cells were selected on carbenicillin (50 µg/ml) and chloramphenicol (34 µg/ml) LB-agarose plates. Single colonies were used to inoculate 5 mL liquid LB medium supplemented with the same antibiotics. The culture was incubated overnight at 37° C. The next day 2 mL of TB medium supplemented with the same antibiotics were inoculated with 0.2 mL of the overnight culture. After 6 hours incubation at 37° C., the culture was cooled down to 28° C. and 1 mM IPTG, 2 mg/mL mevalonate (prepared by dissolving mevalonolactone (Sigma) in 0.5N NaOH at a concentration of 1 g/mL and incubating the solution for 30 min at 37° C.) and 0.2 ml decane were added to each tube. The cultures were incubated for 48 hours at 28° C. The cultures were then extracted twice with 2 volumes of ethylacetate, the organic phase was concentrated to 500 µL and analyzed by GC-MS as described above in Example 3. With the cells producing the (+)-zizaene synthase, the FPP synthase and the four mevalonate pathway enzymes, a productivity of 0.1 mg/mL was obtained and the product profile was identical to the profiles observed with the in-vitro assays (FIG. 3).

This example shows that an *E. coli* cell transformed with a (+)-zizaene synthase, as defined in the present invention, is capable of producing (+)-zizaene. The other enzymes with which the *E. coli* cell is transformed are not essential for the production of (+)-zizaene. Indeed (+)-zizaene is also produced when an *E. coli* cell is transformed with the (+)-zizaene synthase only, but in lower amounts. The other enzymes with which the *E. coli* cell is transformed are added for the only purpose of increasing the amount of precursor available to the (+)-zizaene synthase.

Example 5

Use of the Recombinant VzZS Protein for In-Vivo Production of (+)-Zizaene in Yeast For in-vivo production of sesquiterpenes in yeast cells, a *Saccharomyces cerevisiae* strain (YNP5) in which the ERG9 gene (coding for the squalene synthase, the enzyme converting FPP to squalene) has been down-regulated by replacing the native ERG9 promoter with the MET3 promoter, thus providing a strain with reduced ergosterol biosynthesis and higher FPP pool available for sesquiterpene synthases (Asadollahi, M. A., Maury, J., Moller., K, Nielsen, K. F., Schalk, M., Clark, A., and Nielsen, J., *Biotechnology and Bioengineering* 99(3), 666-677, 2008).

The VzZS cDNA was amplified from the pETDuet-VzZS-opt plasmid with the primers Ctg306_start_opt (SEQ ID NO:16) and Ctg306_stop_opt (SEQ ID NO:17). The PCR was performed with the Pfu DNA Polymerase (Promega) using the following thermal cycling conditions: 90 sec at 94° C.; 35 cycles of 30 sec at 94° C., 30 sec at 55° C. 4 min at 72° C.; and 10 min at 72° C. The amplified cDNA was purified and, in order to add 3' A overhangs, was incubated 15 min at 72° C. in the presence of 0.2 mM dATP and 1 U HotStart Taq DNA polymerase in the appropriate buffer (Qiagen). The cDNA was ligated into pYES2.1/V5-His-TOPO® plasmid using the pYES2.1 TOPO® TA Expression Kit (Invitrogen, Carlsbad, Calif.). The plasmids were selected for correct sequence and orientation of the insert and were used to transform the YNP5 yeast cells using the S.c. EasyComp™ Transformation Kit (Invitrogen, Carlsbad, Calif.).

One single colony of transformed yeast strains were used to inoculate 20 ml of YNB medium (5 g/L $(NH_4)_2SO_4$; 3 g/L $KH_2PO_4$; 0.5 g/L $MgSO_4.7\ H_2O$; 1 mL/L trace metal solution) supplemented with 2% glucose. The culture was incubated for 24 hours at 28° C. The cells were recovered by centrifugation and resuspended in 20 mL of YNB medium supplemented with 2% galactose. After on 1 hour culture, methionine at 0.5 mM final concentration and 2 mL decane were added to the culture. After 24 hours incubation at 28° C., the cultures were extracted with ethyl acetate and analyzed by GC-MS as described in Example 3. The total quantity of sesquiterpenes produced by the yeast cells in these conditions was estimated at 25 mg/L.

What is claimed is:

1. A nucleic acid, which consists of a nucleotide sequence that is identical to SEQ ID NO:2 or SEQ ID NO:11, encoding a polypeptide having a (+)-zizaene synthase activity and having the sequence of SEQ ID NO:1.

2. An expression vector comprising the nucleic acid of claim 1.

3. The expression vector of claim 2, in the form of a viral vector, a bacteriophage or a plasmid.

4. The expression vector of claim 2, including the nucleic acid of the invention operably linked to at least one regulatory sequence which controls initiation or termination of the transcription or translation, with the regulatory sequence including a transcriptional promoter, operator or enhancer or an mRNA ribosomal binding site, and optionally including at least one selection marker.

5. A non-human host organism or cell transformed to harbor at least one nucleic acid according to claim 1 so that it heterologously expresses or over-expresses at least one polypeptide having a (+)-zizaene synthase activity.

6. The non-human host organism of claim 5, which is a plant, a prokaryote, a fungus, a bacteria or a yeast.

7. The non-human host organism of claim 5, wherein the bacteria is *E. coli* and the yeast is *Saccharomyces cerevisiae*.

8. A method for producing (+)-zizaene which comprises:

contacting farnesyl pyrophosphate (FPP) with at least one polypeptide encoded by the nucleic acid of according to claim 1 under conditions sufficient to produce (+)-zizaene; and optionally isolating the (+)-zizaene thus produced.

9. The method of claim 8, which further comprises cultivating a non-human host organism or cell to produce the FPP.

10. The method of claim 9, which further comprises transforming the non human host organism or cell with at least one nucleic acid so that the organism expresses the polypeptide encoded by the nucleic acid.

11. A method for producing at least one polypeptide having a (+)-zizaene synthase activity, which comprises:

culturing a non-human host organism or cell according to claim 5; and isolating the polypeptide from the cultured non-human host organism or cell.

12. The method of claim 11, which further comprises transforming a non-human host organism or cell with at least one nucleic acid encoding a polypeptide having a (+)-zizaene synthase activity, so that the organism expresses the polypeptide encoded by the nucleic acid.

13. A method for preparing a variant polypeptide having a (+)-zizaene synthase activity which comprises:

providing a nucleic acid according to claim 1;

modifying the nucleic acid to obtain at least one mutant nucleic acid;

transforming host cells or unicellular organisms with the mutant nucleic acid sequence to express a polypeptide encoded by the mutant nucleic acid sequence;

screening the polypeptide for at least one modified property;

optionally, if the polypeptide has no desired variant (+)-zizaene synthase activity, repeating the previous steps until a polypeptide with a desired variant (+)-zizaene synthase activity is obtained; and optionally, after a polypeptide having a desired variant (+)-zizaene synthase activity is identified, isolating the corresponding mutant nucleic acid.

14. A polypeptide encoded by the nucleic acid of claim 1 comprising SEQ ID NO: 1.

15. The polypeptide of claim 14, comprising an amino acid sequence that has at least 90% identity to SEQ ID NO: 1.

16. The polypeptide of claim 14, which consists of SEQ ID NO:1.

* * * * *